(12) United States Patent
Xiqin et al.

(10) Patent No.: US 8,380,269 B2
(45) Date of Patent: Feb. 19, 2013

(54) ARRANGEMENT FOR PROVIDING A CONSTANT CONTRACT PRESSURE FOR A PROBE

(75) Inventors: Zhang Xiqin, Singapore (SG); Ting Choon Meng, Singapore (SG)

(73) Assignee: Glucostats System Pte Ltd., Singapore (SG)

( * ) Notice: Subject to any disclaimer, the term of this patent is extended or adjusted under 35 U.S.C. 154(b) by 1007 days.

(21) Appl. No.: 11/991,942

(22) PCT Filed: Aug. 17, 2006

(86) PCT No.: PCT/SG2006/000237
§ 371 (c)(1),
(2), (4) Date: Mar. 17, 2009

(87) PCT Pub. No.: WO2007/032744
PCT Pub. Date: Mar. 22, 2007

(65) Prior Publication Data
US 2009/0216095 A1     Aug. 27, 2009

(30) Foreign Application Priority Data
Sep. 13, 2005     (SG) ................................ 200505849-0

(51) Int. Cl.
*A61B 5/01* (2006.01)
(52) U.S. Cl. ........................................................ 600/316
(58) Field of Classification Search .................. 600/344, 600/316, 322, 323
See application file for complete search history.

(56) References Cited

U.S. PATENT DOCUMENTS 4,183,360 A * 1/1980 Carlson et al. ................ 600/479
5,311,865 A    5/1994 Mayeux

FOREIGN PATENT DOCUMENTS

| JP | 60-15303 | 2/1985 |
|---|---|---|
| JP | 06-116577 | 4/1994 |
| JP | 2001-120521 | 5/2001 |
| JP | 2005-080710 | 3/2005 |
| WO | WO 92/03965 | 3/1992 |
| WO | WO 2004/105596 | 12/2004 |

OTHER PUBLICATIONS

International Search Report for related PCT App. No. PCT/SG2006/000237 dated Oct. 23, 2006.
International Preliminary Report on Patentability for related PCT App. No. PCT/SG2006/000237 dated Sep. 4, 2007.

* cited by examiner

*Primary Examiner* — Max Hindenburg
(74) *Attorney, Agent, or Firm* — Husch Blackwell LLP

(57) ABSTRACT

The invention relates to an arrangement for providing a constant contact pressure for a probe to a finger of a patient, including a housing having a top position and a side portion to support said top portion, said top portion having a thickness defined by a top surface and a base of said top portion, said top portion having a bore extending through, the top portion, said bore dimensioned to slidably receive a probe, said probe having a probe tip, a channel extending substantially perpendicular and on a same plane to said bore, said channel sized to receive a finger of a patient, wherein the probe further includes a collar positioned along the probe such that at rest, the collar is in contact with the top surface of the top portion of the housing, and the probe tip extends a distance from the base of the top portion, and into the channel.

14 Claims, 5 Drawing Sheets

ARRANGEMENT FOR PROVIDING A CONSTANT CONTRACT PRESSURE FOR A PROBE

FIELD OF INVENTION

This invention relates to an arrangement to provide a constant contact pressure for probing, so as to provide a more accurate reading of the subject of the probe. This invention has particular but not exclusive application in probing to establish the blood glucose level of a patient, and may be applicable in cases where a constant contact pressure for a probe is required in the measurement of other physiological parameters of a patient.

BACKGROUND OF THE INVENTION

Hyperglycemia or abnormally high glucose levels, occurs when the body has too little insulin, or when the body cannot use insulin properly. It occurs in people with diabetes and if left untreated, this condition can lead to coma or death.

Patients with diabetes are therefore required to regularly monitor their blood glucose levels, so as to manage food intake and the dosage and timing of insulin injection.

There are presently various methods adopted to allow patients to monitor their blood glucose levels, and are broadly grouped into two broad categories—invasive and non-invasive.

Invasive Monitoring

Invasive blood monitoring is by analysing the blood of a patient. This is usually done by obtaining a drop of blood, usually from the finger. This blood is then placed on a strip containing reagents that react with glucose to form a chromophor. This is subsequently read by a reflectance calorimeter within an analyser, to determine the level of glucose present in the blood.

The blood is obtained by the use of lancets, laser sensors (known commercially as Lasettes), or silicon micro-needles, just to name a few.

However, as patients need to check their blood glucose levels usually several times a day, invasive monitoring methods are not ideal. More importantly, the used needles or lancets may cause contamination, and should be treated as bio-hazards. Used needles or lancets must be disposed of properly.

Non-invasive Monitoring

Non-invasive monitoring techniques and methods are preferred, as these methods do not cause physical injury, nor do they contribute to the stress and discomfort to a patient.

The current non-invasive monitors include the following:
a. Interstitial fluid monitors that are depressed against the skin to obtain a glucose reading. However, glucose levels in interstitial fluid may lag a few minutes behind those of capillary blood. Therefore, the readings obtained are not real time information, which may be crucial.
b. Glucose sensing lenses, which are used together with a near infrared energy source. This energy illuminates the eye, and is passed through the aqueous human in the anterior chamber of the eye and then reflected from the iris. The reflected energy is collected for analysis, and is an indication of the glucose concentration in the patient's blood. However, this method though technically non-invasive, can hardly be said to be non-obtrusive.
c. Optical absorption technique, in which an incident infrared light source is delivered through an optical fibre to a probe for measurement. On the same probe, there is corresponding optical fibre to deliver the diffused light from the point of measurement to a photo diode for subsequent data processing.

Of these 3 approaches, the optical absorption technique for quantification of glucose using infrared light source has demonstrated to be a very promising approach for non-invasive blood glucose sensing.

However, a huge drawback of this technique is that when the probe comes in contact with the body surface, a major problem arises from contact pressure. The contact pressure however small will have an influence on the body tissue compression (immediately beneath the skin/nail) and hence will affect the blood flow. For instance, a large contact pressure of the probe can result in occluding the flow on tissue (immediately beneath the skin) and blood flow, leading to tissue blanching.

In the optical absorption technique for non-invasive blood glucose sensing, an incident infrared light is directed through the skin/nail and is absorbed by blood (glucose) that is immediately beneath. Therefore, if the blood flow beneath the skin/nail varies due to varying contact pressure, then a fluctuating signal output is inevitable. The signal output is received by an infrared sensor, (or photodiode) which is very sensitive. A small variation of contact pressure is known to create a large fluctuation in the signal output.

In non-invasive blood glucose sensing application, the probe is expected to be applied repeatedly for measurement at the convenience of the user. Hence variation of contact pressure of the probe in repeated measurements is known to cause large fluctuation in signal output leading to high uncertainty or inaccuracy of the actual blood glucose reading of a patient.

It is an object of the present invention to overcome or at least ameliorate one or more of the above problems in the prior art.

Discussion of any one of the prior art mentioned above is not to be taken as an admission of the state of common general knowledge of the skilled addressee.

SUMMARY OF THE INVENTION

According to the invention, there is provided an arrangement for providing a constant contact pressure for a probe to a finger of a patient, including a housing having a top portion and a side portion to support said top portion, said top portion having a thickness defined by a top surface and a base of said top portion, said top portion having a bore extending through the top portion, said bore dimensioned to slidably receive a probe, said probe having a probe tip, a channel extending substantially perpendicular and on a same plane to said bore, said channel sized to receive a finger of a patient, wherein the probe further includes a collar positioned along the probe such that at rest, the collar is in contact with the top surface of the top portion of the housing, and the probe tip extends a distance from the base of the top portion, and into the channel.

In the embodiment, when in use, a finger of a patient is introduced into the channel, and to contact the probe tip, and upon said contact, the probe is urged upwards along the bore, so that the probe tip rests on the finger of a patient, and the collar is lifted off the top surface of the top portion so that the collar acts as a constant weight on the probe resting on a finger of a patient.

Preferably, the distance of the probe tip from the base of the top portion, when the collar is resting on the top surface of the top portion, is around 5 mm.

In a preferred embodiment, the channel further includes an end stop to provide a guide to a finger tip of a patient, the end stop provided at a position where when the finger tip contacts the end stop, the patient's finger nail is below the bore, so that the probe tip may contact a finger nail of a patient.

Preferably, the end stop is concave in profile, so that it follows the contours of a finger tip for the comfort of a patent.

In a preferred embodiment, the channel is in the housing.

Preferably, the collar is screw threaded, and an exterior surface of the probe is provided with threads, so that the position of the collar along the probe may be adjusted.

Still preferably, the entrance of the channel is adjustable so that it can fit a patient's finger of various sizes.

In a preferred embodiment, the exterior surface of the probe further includes friction reducing agents.

In another preferred embodiment, the bore further includes friction reducing agents.

Preferably, the bore is circular to suit the profile of a probe.

In a preferred embodiment, the probe has sensors therewithin.

Preferably, the sensors are light transmissive and light receptive opical fibres.

Still preferably, the sensors are coupled to an analyzer to establish a physiological parameter of a patient.

Preferably, the analyzer is a photosensor.

Preferably, the light transmissive and light receptive fibres are mutually optically insulated.

DESCRIPTION OF FIGURES

In order that the invention might be more fully understood, embodiments of the invention will be described by way of example only, with reference to the accompanying drawings, in which.

The attached drawings are not necessarily drawn to scale.

DESCRIPTION OF EMBODIMENTS OF THE INVENTION

Reference will now be made in detail to the preferred embodiments of the invention, examples of which are illustrated in the accompanying drawings. The preferred embodiments of the invention are not intended to limit the invention in its broadest aspect to these embodiments. On the contrary, the invention is intended to cover alternatives, modifications and equivalents, which may be included within the spirit and scope of the invention as defined by the appended claims. Furthermore, in the following detailed description of the embodiments, numerous specific details are set forth in order to provide an understanding of the present embodiments.

The invention relates to an arrangement for providing a constant contact pressure, required when probing a patient, to obtain a physiological parameter of the patient. References to the invention in the following paragraphs are described in the application for blood glucose probe measurement. However, it is to be understood that the references are merely examples of a particular application of this invention, and are not intended to form the sole purpose and application of the present invention.

The probe region is described as a fingernail in the following paragraphs. However, it is to be understood that the probe region may reside in other areas of a patient. Probing of the fingernail region is advantageous because it provides a firm surface for the probe to come in contact with. Also, contact with the fingernail does not depress the capillaries underneath straightaway. Therefore, blood flow through the capillaries under the nail will not be interrupted.

Figure 1:
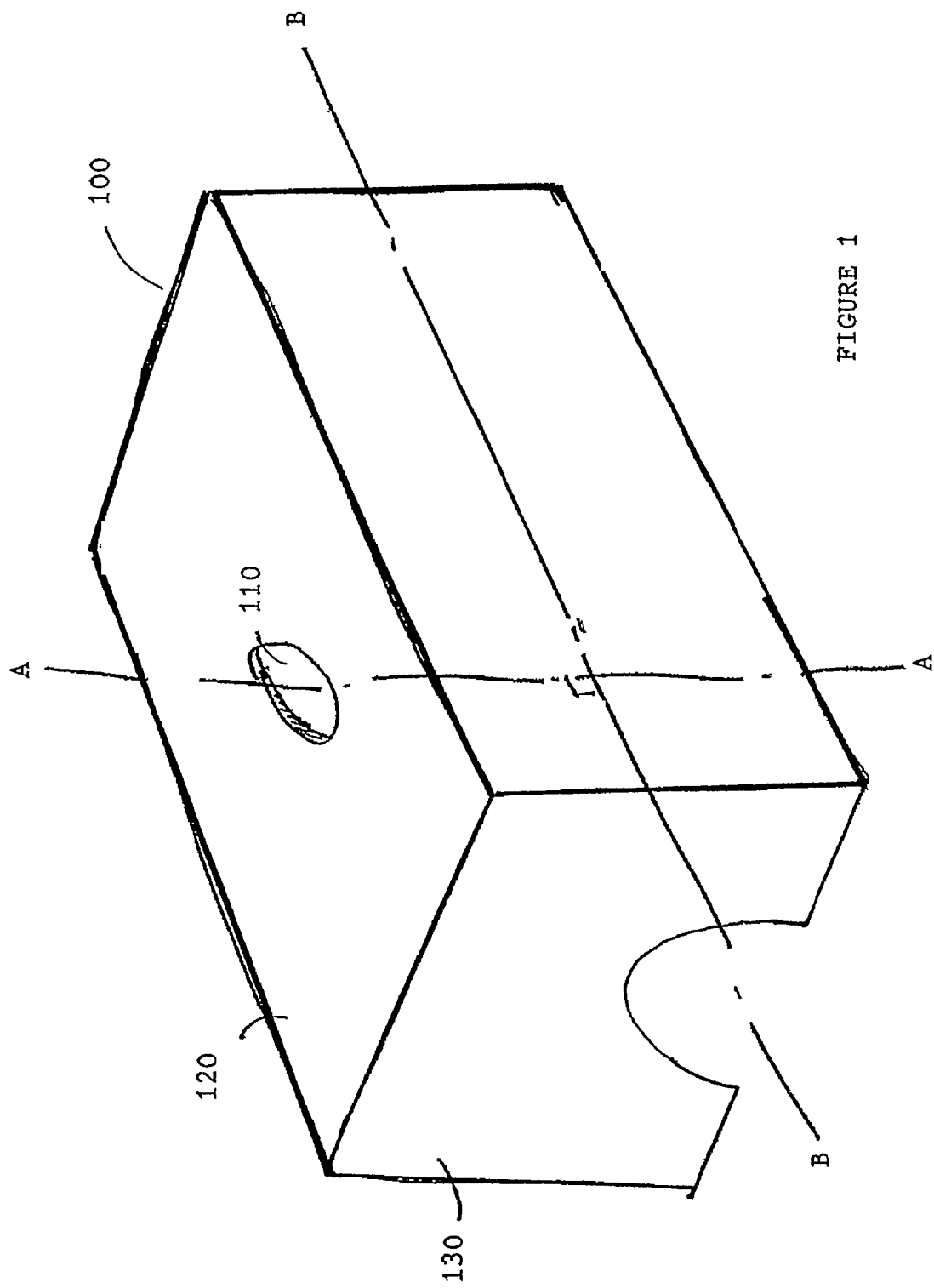
FIG. 1 shows a perspective view of a preferred embodiment of the housing of the arrangement.

Referring to FIG. 1, the arrangement includes a housing 100 having a top portion 120 and a support portion in the form of a side portion 130. The housing 100 further includes a circular bore 110 extending through a thickness x, of the top portion 120. The circular bore 110 is dimensioned to receive a probe and preferably inhibit lateral movement of the probe once it is received therein. When the probe is placed through the circular bore 110, the longitudinal axis of the probe A-A is aligned generally perpendicular to the top surface 120.

The housing 100 further includes a channel 40 therethrough. The channel 40 is positioned such that its longitudinal axis B-B is perpendicular to the longitudinal axis of the probe A-A.

Figure 2:
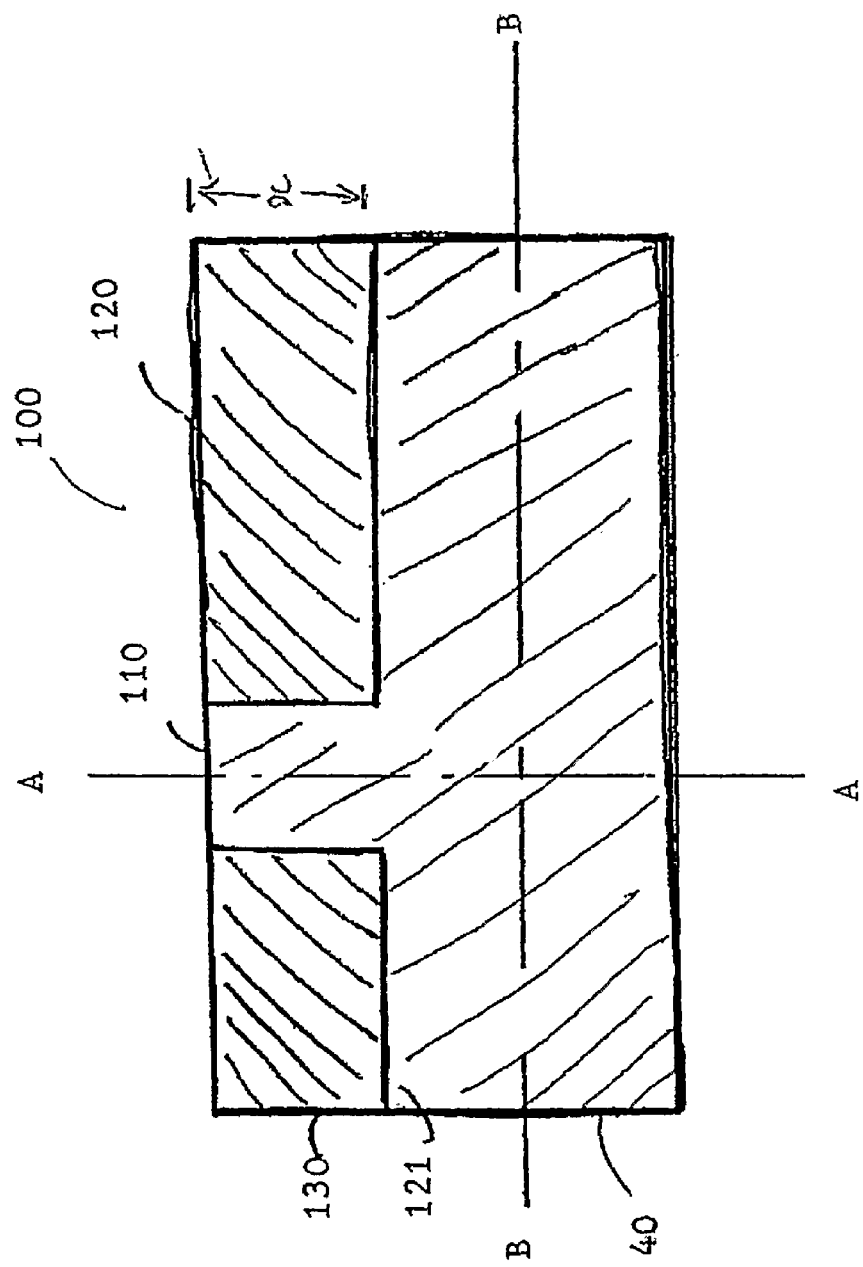
FIG. 2 shows a side cut-through view of the preferred embodiment of the housing of the arrangement.

FIG. 2 shows a side elevation of an embodiment of the housing of the arrangement.

The purpose of the arrangement is to allow a constant contact pressure of a probe, to be achieved.

Figure 3:
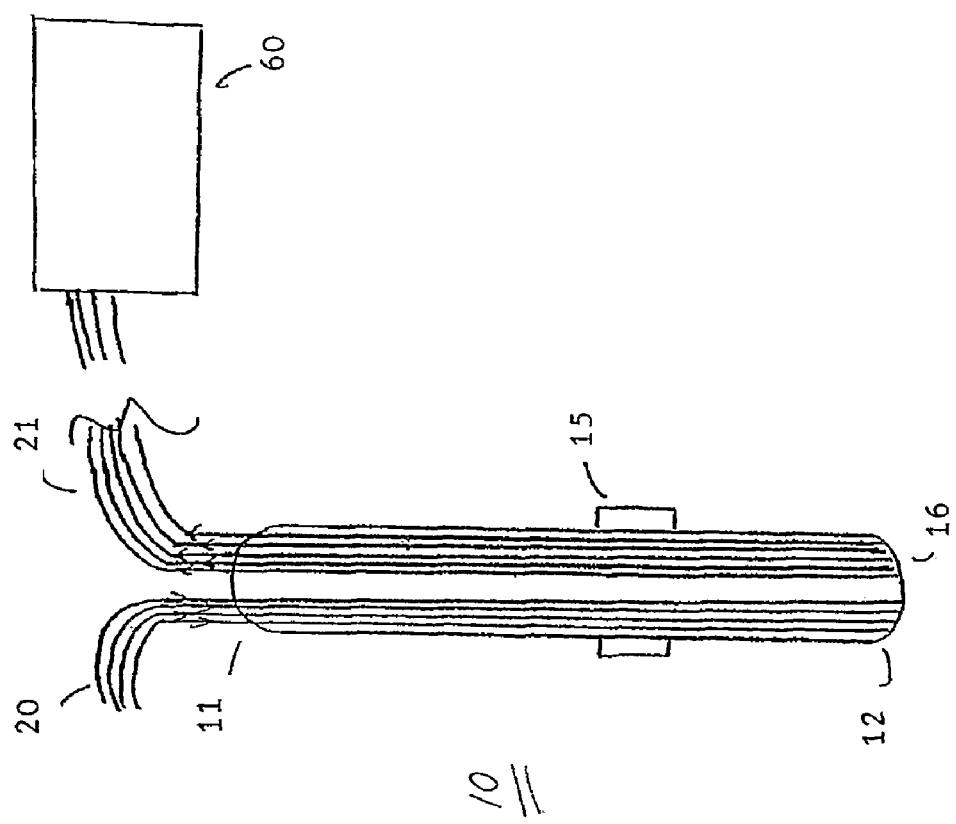
FIG. 3 shows a preferred embodiment of the probe used in the arrangement.

The probe 10, as seen in FIG. 3 has sensors therewithin, responsive to a patient's physiological parameter. In the present embodiment, the sensors are in the form of light transmissive 20 and light receptive 21 optical fibres. The light transmissive optical fibres 20, are coupled from an infrared light source, and the light receptive optical fibres 21, are coupled to an analyser, or a photosensor 60, to establish a blood glucose level of the patient.

The light transmissive and light receptive optical fibres may be mutually optically insulated, to eradicate the possibility of any light interference. The probe 10 has a proximal end 11 connected to the analyser or photosensor 60, and a distal end 12, where the probe tip 16 is located.

The probe 10 in the arrangement of the present invention further includes a positioning means 14, in the form of a collar 15. The collar 15 is sized so as to be attached to the probe. In this way, the outer diameter of the collar is enlarged in relation to the annular bore 110. When the collar 15 is fixed to the probe, the physical interaction of the collar with the top surface 120, will inhibit further downward movement of the probe. Once the collar 15 contacts the top surface 120, the collar will inhibit further downward movement of the probe, and functions like a stopper.

The resting position of the collar 15 is such that the length of probe from the probe tip, to the base of the collar 15, is slightly more than the thickness of the top portion 120. It is preferred that the position of the collar 15 is x+5 mm from the probe tip, the relevance will be apparent later.

Figure 4:
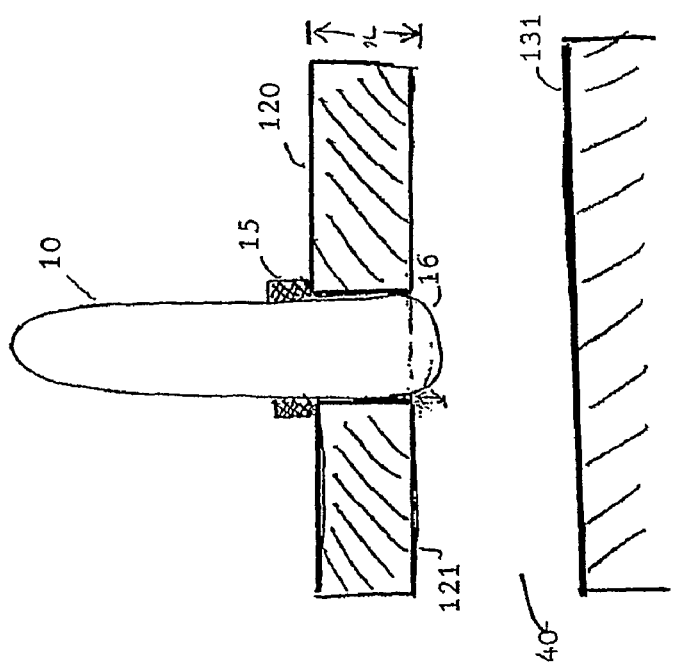
FIG. 4 shows a side cut-through view of the preferred embodiment of the arrangement when not in use.

FIG. 4 shows the arrangement with the probe 10 in the circular bore. As can be seen in FIG. 4, the collar 15 is affixed to the probe 10, and rests on the top surface of the top portion 120. The collar 15 prevents further downward movement of the probe 10, into the channel 40. In the embodiment of FIG. 4, the probe tip 16 extends about 5 mm from the base of the top portion 121. When the collar 15 is not resting on the top portion, the weight of the collar also functions as a constant weight to the probe 10.

The base of the top portion 121, and the base of the bottom portion 131 is spaced apart to accomplish a certain thickness. In the present embodiment, the thickness derived is the thickness of a patient's finger. An allowance may be provided so that a patient's finger may slide in and out with ease, during which time no pressure should be exerted on the finger 50.

Any pressure exerted on a patent near the probe region is to be avoided, as this may cause blanching of the tissue in the area. This will affect the readings that may be obtained from the sensor, resulting in inaccurate readings.

Figure 5:
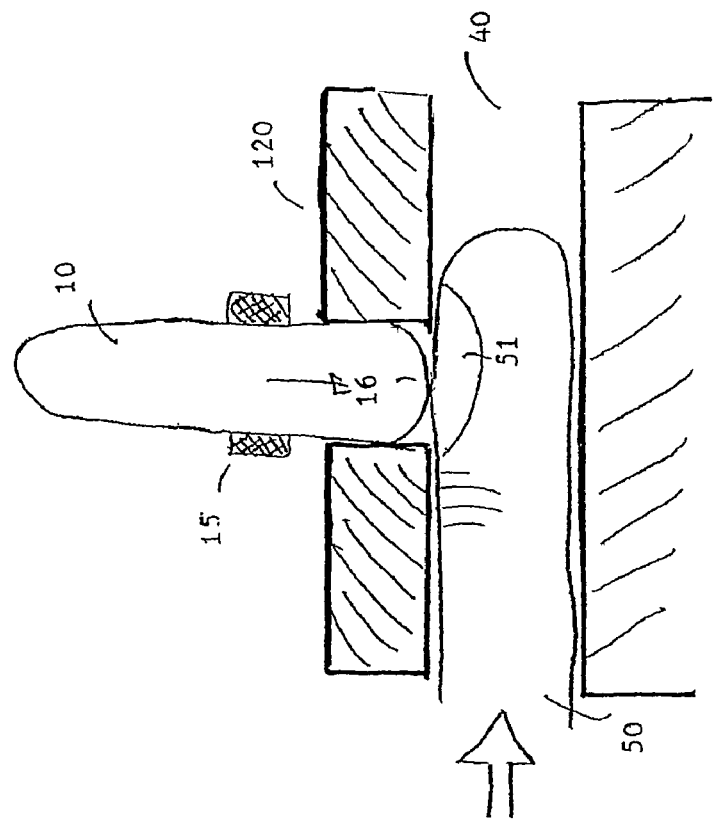
FIG. 5 shows a side cut-through view of one preferred embodiment of the arrangement when in use.

FIG. 5 shows the arrangement when in use. As previously described, the collar 15 is positioned so that the probe tip preferably extends 5 mm into the channel 40. A patient's finger 50 is inserted through the channel 40 and moved forward until it touches the side of the probe tip 16. Further forward motion of the finger 50 transmits a relative transverse force, and urges the probe tip 16 upwards so that the patient's finger can continue forward. This is possible as the contour of a finger is of a gradual inclination, and the extension of the probe tip is minimal. Therefore, the length of extension beyond the base 121, is such that a transverse force applied by a patient's finger will cause the probe 10 to move upwards along the bore 110, and finally rest on the surface of a patient's fingernail. When in this position, the probe tip 16 is in surface contact with the patient's fingernail 51. In this position of the probe 10, the collar 15 is lifted off the surface 120, and the weight of the collar together with the probe enacts onto a patient's nail 51. Therefore, the collar 15, functions also as a weight, to enact a constant downward force to the probe region. As can be appreciated, the weight of the collar and the probe itself is of constant weight, and therefore the arrangement provides a constant contact pressure to be achieved for the probe. The weight of the collar 15 cannot be too substantial, as it may occlude blood flow to the region, which may interfere with the readings obtained through the probe 10. As can be appreciated, the collar acts as a constant weight to the probe, which allows a constant pressure probe to be performed on a patient. The weight of the collar enacts enough pressure on a patient's finger for probing to be performed, the constant weight advantageously allows repeatability of readings. This leads to higher consistency in the readings taken from a patient.

Figure 6:
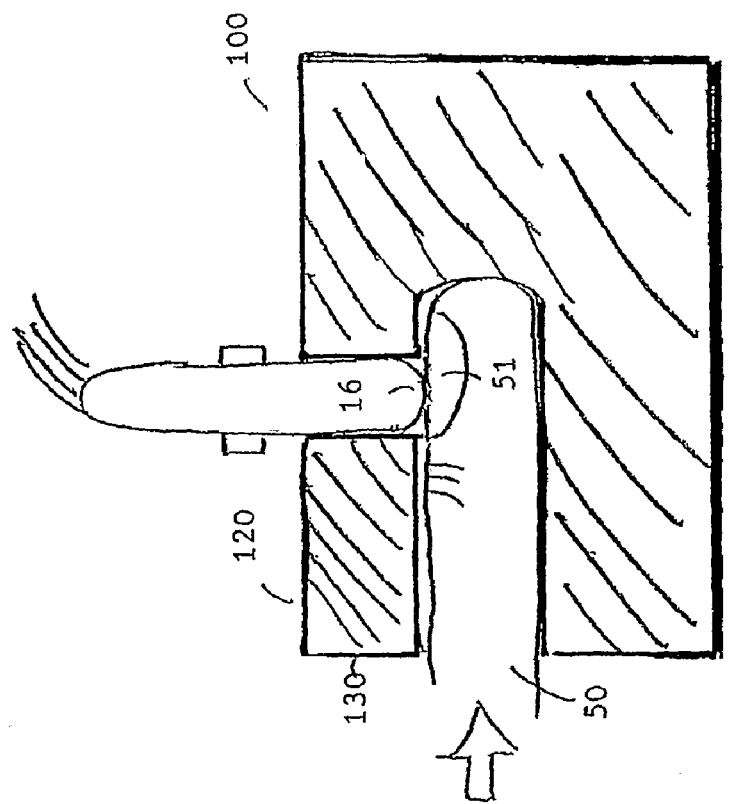
FIG. 6 shows a side cut-through view of a second preferred embodiment of the arrangement when not in use.

FIG. 6 shows a second embodiment of the housing, where a recess 41, acting as an end stop, is introduced into the channel. In this embodiment, the channel does not extend throughout the housing 100, but terminates shortly after the position of the circular bore 110. This is advantageous as a patient will not further extend his finger inward once the end stop is reached. At this position, the fingernail will be directly underneath the probe tip, so that probing may be performed. The end stop is shown as a recess 41, and may be concave in profile, so that it follows the contours of a finger tip.

Figure 7:
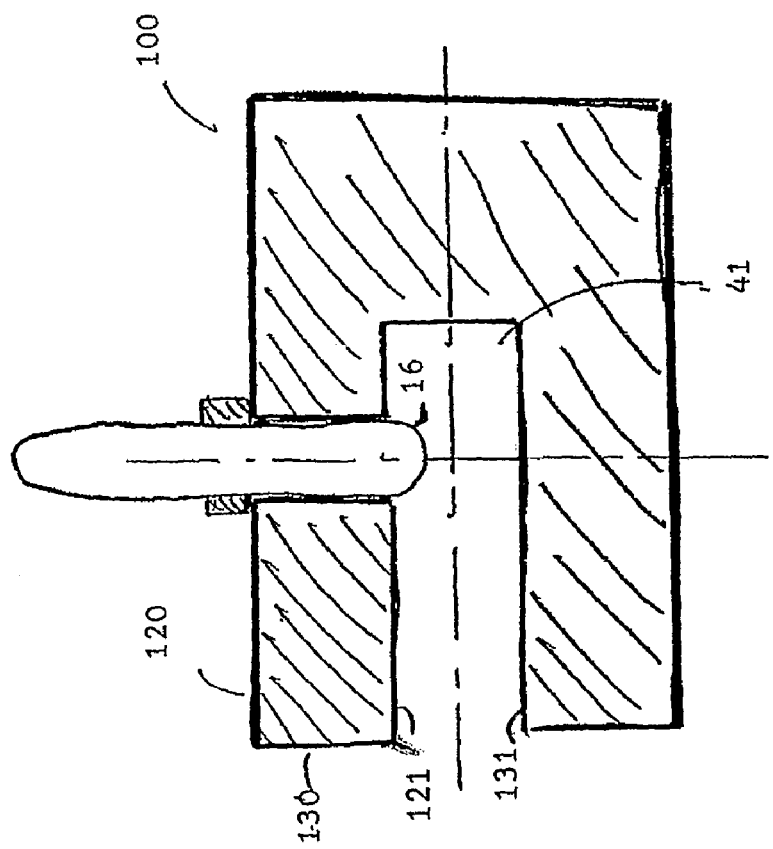
FIG. 7 shows a side cut-through view of the second embodiment of the arrangement when in use.

FIG. 7 shows the side elevation of the second embodiment, when the arrangement is used. The end stop advantageously provides an indication of the positioning of the finger within the housing, relative to the probe tip, so that the probe region is standardised.

In another embodiment, the collar may be internally screw threaded, and the exterior surface of the probe may be provided with threads, so that the position of the collar along the longitudinal axis of the probe may be adjusted to accommodate various thickness of the top surface 120 and when not supported by the top surface 120.

In a further embodiment, the size of the entrance to the channel, may be made adjustable, so that it can fit patient's fingers of various sizes.

In a still further embodiment, the circular bore and/or the exterior surface of the probe may be coated with friction reducing agents, or lubricants, so that the probe may slide freely along the thickness of the bore.

The embodiments have been advanced by way of example only, and modifications are possible within the scope of the invention as defined by the appended claims.

The invention claimed is:

1. An apparatus for repeatedly providing a probe in contact with a human finger with the same pressure each time comprising:
   a. a housing having a top surface and having a first passage of a size and shape such as to receive and accommodate a finger therein;
   b. said housing further including a second passage extending downwardly from said top surface substantially perpendicular to said first passage and in communication therewith; and
   c. a probe of a predetermined weight and a collar on said probe freely slidable in said second passage, said probe having a sensor for obtaining a physiological parameter from said finger, whereby said probe engages the finger with the same downward force each time the probe contacts the finger by the predetermined weight of the probe and collar.

2. An apparatus as claimed in claim 1 further comprising said collar having a diameter larger than the diameter of said second passage and positioned along the probe.

3. An apparatus as claimed in claim 1 wherein a tip of the probe is extended substantially 5 mm from said top surface.

4. An apparatus as claimed in claim 1 wherein said first passage further includes an end stop to provide a guide to a finger tip of a patient, the end stop provided where the patient's finger nail is below the second passage, so that the probe tip may contact a finger nail of a patient when the finger tip contacts the end stop.

5. An apparatus as claimed in claim 1 wherein the end stop is concave in profile, so that it follows the contours of a finger tip.

6. An apparatus as claimed in claim 1 wherein the collar is screw threaded, and an exterior surface of the probe is provided with threads, so that the position of the collar along the probe may be adjusted.

7. An apparatus as claimed in claim 1 wherein the entrance of said first passage is adjustable so that it can fit a patient's finger of various sizes.

8. An apparatus as claimed in claim 1 wherein the exterior surface of said probe further includes friction reducing agents.

9. An apparatus as claimed in claim 1 wherein said second passage further includes friction reducing agents.

10. An apparatus as claimed in claim 1 wherein the second passage is circular.

11. An apparatus as claimed in claim 1 wherein the sensors in the probe are light transmissive and light receptive optical fibres.

12. An apparatus as claimed in claim 1 wherein said sensor is coupled to an analyzer.

13. An apparatus as claimed in claim 12 wherein the analyzer is a photosensor.

14. An apparatus as claimed in claim 11 wherein the light transmissive and light receptive fibres are mutually optically insulated.

* * * * *

UNITED STATES PATENT AND TRADEMARK OFFICE
CERTIFICATE OF CORRECTION

| | |
|---|---|
| PATENT NO. | : 8,380,269 B2 |
| APPLICATION NO. | : 11/991942 |
| DATED | : February 19, 2013 |
| INVENTOR(S) | : Zhang Xiqin and Ting Choon Meng |

It is certified that error appears in the above-identified patent and that said Letters Patent is hereby corrected as shown below:

On the title page, item (54) and in the specification, column 1, line 1, delete the current title:
"ARRANGEMENT FOR PROVIDING A CONSTANT CONTRACT PRESSURE FOR A PROBE"
and, insert the following title:
--ARRANGEMENT FOR PROVIDING A CONSTANT CONTACT PRESSURE FOR A PROBE--.

Col. 3, line 5, delete the word "patent", and insert --patient--.

Col. 5, line 7, delete the word "patent", and insert --patient--.

Signed and Sealed this
Fifth Day of November, 2013

Teresa Stanek Rea
*Deputy Director of the United States Patent and Trademark Office*